United States Patent
Steadman Booker et al.

(10) Patent No.: US 11,662,482 B2
(45) Date of Patent: May 30, 2023

(54) X-RAY DETECTOR COMPRISING AT LEAST ONE LIGHT EMITTING LAYER

(71) Applicant: KONINKLIJKE PHILIPS N.V., Eindhoven (NL)

(72) Inventors: Roger Steadman Booker, Aachen (DE); Walter Ruetten, Linnich (DE); Matthias Simon, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/780,500

(22) PCT Filed: Dec. 2, 2020

(86) PCT No.: PCT/EP2020/084219
§ 371 (c)(1),
(2) Date: May 26, 2022

(87) PCT Pub. No.: WO2021/115865
PCT Pub. Date: Jun. 17, 2021

(65) Prior Publication Data
US 2022/0365230 A1 Nov. 17, 2022

(30) Foreign Application Priority Data
Dec. 9, 2019 (EP) .................................. 19214388

(51) Int. Cl.
*A61B 6/00* (2006.01)
*A61B 6/03* (2006.01)
*G01T 1/20* (2006.01)

(52) U.S. Cl.
CPC .......... *G01T 1/20181* (2020.05); *A61B 6/032* (2013.01); *A61B 6/4208* (2013.01);
(Continued)

(58) Field of Classification Search
CPC .......... A61B 6/032; A61B 6/037; A61B 6/42; A61B 6/4208; A61B 6/4233;
(Continued)

(56) References Cited

U.S. PATENT DOCUMENTS 4,437,006 A * 3/1984 Morgan ............... A61B 6/4241
250/363.02
4,511,799 A * 4/1985 Bjorkholm ............ G01T 1/2018
250/370.06
(Continued)

FOREIGN PATENT DOCUMENTS

JP 2015137882 A 7/2015
KR 20080092393 A 10/2008
(Continued)

OTHER PUBLICATIONS

PCT International Search Report, International application No. PCT/EP2020/084219, dated Feb. 19, 2021.

*Primary Examiner* — Allen C. Ho
(74) *Attorney, Agent, or Firm* — Larry Liberchuk

(57) ABSTRACT

An X-ray detector comprises a first scintillator layer, a second scintillator layer, a first photodiode array, a second photodiode array, and at least one light emitting layer. The first scintillator layer is configured to absorb X-rays from an X-ray pulse and emit light. The first photodiode array is positioned adjacent to the first scintillator layer and is configured to detect at least some of the light emitted by the first scintillator layer. The second scintillator layer is configured to absorb X-rays from the X-ray pulse and emit light. The second photodiode array is positioned adjacent to the second scintillator layer and is configured to detect at least some of the light emitted by the second scintillator layer. The at least one light emitting layer is configured to emit radiation such that at least some of the emitted radiation (Continued)

irradiates the first photodiode array, and at least some of the emitted radiation irradiates the second photodiode array.

14 Claims, 4 Drawing Sheets

(52) U.S. Cl.
CPC ............ *A61B 6/4241* (2013.01); *A61B 6/482* (2013.01); *G01T 1/2002* (2013.01); *G01T 1/2006* (2013.01); *G01T 1/2008* (2013.01); *G01T 1/2018* (2013.01); *G01T 1/20183* (2020.05); *G01T 1/20184* (2020.05); *G01T 1/20186* (2020.05); *G01T 1/20187* (2020.05); *G01T 1/20188* (2020.05)

(58) Field of Classification Search
CPC ......... A61B 6/4241; A61B 6/482; A61B 6/54; A61B 6/542; A61B 6/545; G01T 1/20; G01T 1/2002; G01T 1/2006; G01T 1/2008; G01T 1/2018; G01T 1/20181; G01T 1/20182; G01T 1/20183; G01T 1/20184; G01T 1/20185; G01T 1/20186; G01T 1/20187; G01T 1/20188
USPC ................. 378/19, 98.8, 98.9, 5; 250/370.09
See application file for complete search history.

(56) References Cited

U.S. PATENT DOCUMENTS

| | | | |
|---|---|---|---|
| 5,025,462 A | 6/1991 | Saito | |
| 5,548,123 A * | 8/1996 | Perez-Mendez | G01T 1/2018 250/370.11 |
| 6,031,892 A * | 2/2000 | Karellas | A61B 6/4258 250/370.11 |
| 6,954,514 B2 * | 10/2005 | Wischmann | G01T 1/2018 250/370.15 |
| 7,263,165 B2 * | 8/2007 | Ghelmansarai | G01T 1/2018 250/370.11 |
| 7,286,640 B2 * | 10/2007 | Yun | G01T 1/202 250/370.11 |
| 7,375,341 B1 * | 5/2008 | Nagarkar | G01T 1/2002 250/370.11 |
| 7,381,956 B2 * | 6/2008 | Overdick | G01T 1/2018 250/361 R |
| 7,388,208 B2 | 6/2008 | Deych | |
| 7,626,389 B2 * | 12/2009 | Fiedler | G01R 33/28 324/309 |
| 7,671,342 B2 * | 3/2010 | Bani-Hashemi | G01T 1/2008 378/92 |
| 7,696,481 B2 * | 4/2010 | Tkaczyk | G01T 1/2985 250/363.02 |
| 7,834,321 B2 * | 11/2010 | Yorkston | G21K 4/00 250/370.09 |
| 7,929,665 B2 * | 4/2011 | Kang | G01T 1/2018 250/370.11 |
| 7,968,853 B2 * | 6/2011 | Altman | A61B 6/032 250/366 |
| 8,338,789 B2 * | 12/2012 | Takihi | G01T 1/2008 250/366 |
| 8,391,439 B2 * | 3/2013 | Levene | G01T 1/2985 378/19 |
| 8,440,977 B2 | 5/2013 | Ishii | |
| 8,442,184 B2 * | 5/2013 | Forthmann | A61B 6/032 378/5 |
| 8,466,421 B2 * | 6/2013 | Virshup | G01T 1/208 250/367 |
| 8,525,121 B2 * | 9/2013 | Nakatsugawa | H01L 27/14663 257/E31.129 |
| 8,648,312 B2 * | 2/2014 | Ichimura | G01T 1/202 250/367 |
| 8,653,471 B2 * | 2/2014 | Proksa | A61B 6/4208 250/363.01 |
| 8,723,129 B2 * | 5/2014 | Suyama | B82Y 10/00 250/361 R |
| 8,729,478 B2 * | 5/2014 | Tredwell | G01T 1/2018 250/362 |
| 8,772,728 B2 * | 7/2014 | Tredwell | G01T 1/2018 250/370.01 |
| 8,835,860 B2 * | 9/2014 | Wu | G01T 1/2018 250/366 |
| 8,873,713 B2 * | 10/2014 | Suyama | G01N 23/04 378/98.12 |
| 8,903,046 B2 * | 12/2014 | Morton | G01V 5/0041 378/87 |
| 8,981,310 B2 * | 3/2015 | Suyama | G01N 23/087 378/98.12 |
| 9,012,857 B2 * | 4/2015 | Levene | G01T 1/2018 378/19 |
| 9,093,347 B2 * | 7/2015 | Watanabe | H01L 27/14663 |
| 9,182,508 B2 | 11/2015 | Wallace | |
| 9,526,466 B2 * | 12/2016 | Karim | H01L 27/14663 |
| 9,678,222 B2 | 6/2017 | Snoeren | |
| 9,995,831 B2 * | 6/2018 | Verschuren | G01T 1/2002 |
| 10,234,572 B2 * | 3/2019 | Hadjioannou | G01T 1/20 |
| 10,444,378 B1 * | 10/2019 | Morf | H01L 27/14658 |
| 10,459,094 B2 * | 10/2019 | Simanovsky | G01T 1/2018 |
| 10,754,047 B2 * | 8/2020 | Shimizukawa | G01T 1/2018 |
| 10,761,219 B2 | 9/2020 | Deych | |
| 10,768,317 B2 * | 9/2020 | Tateishi | A61B 6/4233 |
| 10,838,079 B2 * | 11/2020 | Shimizukawa | A61B 6/4283 |
| 10,881,366 B2 * | 1/2021 | Taninai | A61B 6/4233 |
| 11,000,701 B2 * | 5/2021 | Lu | A61N 5/1039 |
| 11,016,202 B2 * | 5/2021 | Morf | H01L 27/14663 |
| 11,041,966 B2 * | 6/2021 | Chappo | A61B 6/4241 |
| 11,156,727 B2 * | 10/2021 | Shedlock | G01T 1/2018 |
| 11,209,556 B2 * | 12/2021 | Wimmers | G01T 1/1663 |
| 11,243,313 B2 * | 2/2022 | Takenaka | G01T 1/20181 |
| 11,307,325 B2 | 4/2022 | Morton | |
| 11,346,962 B2 * | 5/2022 | Ullah | G01T 1/2008 |
| 11,428,830 B2 * | 8/2022 | Van De Haar | G01T 1/1611 |
| 2003/0043959 A1 | 3/2003 | Wischmann | |
| 2011/0303849 A1 | 12/2011 | Tredwell | |
| 2012/0106698 A1 | 5/2012 | Karim | |
| 2012/0168633 A1 | 7/2012 | Tredwell | |
| 2014/0021372 A1 | 1/2014 | Suyama | |
| 2014/0339431 A1 | 11/2014 | Watanabe | |
| 2019/0353802 A1 | 11/2019 | Steinhauser | |

FOREIGN PATENT DOCUMENTS

| | | |
|---|---|---|
| WO | WO2011135486 A | 11/2011 |
| WO | WO2012147814 A1 | 11/2011 |
| WO | WO2011135486 A3 | 11/2012 |
| WO | WO2012147814 A1 | 11/2012 |

* cited by examiner

X-RAY DETECTOR COMPRISING AT LEAST ONE LIGHT EMITTING LAYER

FIELD OF THE INVENTION

The present invention relates to an X-ray detector, and to an X-ray detector system.

BACKGROUND OF THE INVENTION

Specialized X-ray detectors for spectral energy computer tomography and/or X-ray applications, comprising two or more scintillator layers and associated photo diode arrays, are very expensive. Low-cost photodiodes, for example based on an organic layer—OPD—or amorphous silicon (a-Si), have a relatively high defect density in the bulk, where charge can be trapped at defect sites and released at a later time. Because of such an issue leading to image artefacts, these detectors cannot find utility in these specialized applications.

There is a need to address this issue.

SUMMARY OF THE INVENTION

It would be advantageous to have an ability to utilize low-cost photodiodes in specialized multiple layer X-ray detectors. The object of the present invention is solved with the subject matter of the independent claims, wherein further embodiments are incorporated in the dependent claims. It should be noted that the following described aspects and examples of the invention apply also to the X-ray detector and to the X-ray detector system.

In a first aspect, there is provided an X-ray detector comprising two or more scintillator layers, comprising:
 a first scintillator layer;
 a second scintillator layer;
 a first photodiode array;
 a second photodiode array; and
 at least one light emitting layer.

The first scintillator layer is configured to absorb X-rays from an X-ray pulse and (in response thereto) to emit light. The first photodiode array is positioned adjacent to the first scintillator layer. The first photodiode array is configured to detect at least some of the light emitted by the first scintillator layer. The second scintillator layer is configured to absorb X-rays from the X-ray pulse passing through the first scintillator layer and (in response thereto) to emit light. The second photodiode array is positioned adjacent to the second scintillator layer. The second photodiode array is configured to detect at least some of the light emitted by the second scintillator layer. The at least one light emitting layer is configured to emit radiation such that at least some of the emitted radiation irradiates the first photodiode array and at least some of the emitted radiation irradiates the second photodiode array.

The X-ray pulses passing through the first scintillator layer and being absorbed by the second scintillator layer typically have higher energy than the X-ray pulses being absorbed in the first scintillator layer. In this manner, a dual layer detector with energy-discriminating scintillator layers for example for computed tomography dual energy applications, can utilize low-cost photodiodes (based on for example an organic layer OPD or a-Si). This is because although these low-cost photodiodes have a relatively high defect density in the bulk, a light emitting layer is provided that can for example emit visible and ultraviolet light below 750 nm to fill defect sites, or infrared radiation for example above 750 nm to fill traps within the bandgap. This means that problems such as a change in effective gain (or detective efficiency) and/or a change in the step response for such low-cost detectors is mitigated.

The first photodiode array being positioned adjacent to the first scintillator layer does not preclude another element of the X-ray detector being between the first photodiode array and the first scintillator layer.

The second photodiode array being positioned adjacent to the second scintillator layer does not preclude another element of the X-ray detector being between the second photodiode array and the second scintillator layer.

In an example, the at least one light emitting layer is configured to emit radiation at infrared wavelengths, and/or the at least one light emitting layer is configured to emit radiation at visible and/or the at least one light emitting layer is configured to emit radiation at ultraviolet wavelengths.

In an example, the at least one light emitting layer is positioned between the first photodiode array and the second photodiode array.

In this manner, only one light emitting layer is required, that can emit radiation in one direction to radiate the first photodiode and emit radiation in the counter direction to radiate the second photodiode array.

The at least one light emitting layer being positioned between the first photodiode array and the second photodiode array does not preclude another element of the X-ray detector being between the at least one light emitting layer and the first photodiode array.

The at least one light emitting layer being positioned between the first photodiode array and the second photodiode array does not preclude another element of the X-ray detector being between the at least one light emitting layer and the second photodiode array.

In an example, the at least one light emitting layer is configured such that a transmission of the at least one light emitting layer in a direction from the first photodiode array to the second photodiode array for light emitted by the first scintillator layer and/or in a direction from the second photodiode array to the first photodiode array for light emitted by the second scintillator layer is less than 10%, preferable less than 5%, more preferably less than 1%.

This means that crosstalk from one scintillator layer to the other scintillator layer is minimized, because radiation emitted by a scintillator layer cannot (or at least the majority of radiation cannot) cross the layer and be collected by the photodiode array associated with the other scintillator layer.

In an example, a first light emitting layer is positioned below the first photodiode array and a second light emitting layer is positioned below the second photodiode array.

Here, below means on a side of the first photodiode array away from the source of X-rays.

In this manner, crosstalk can be completely eliminated because one light emitting layer is positioned between the two scintillator layers, and a bottom surface of that light emitting layer can be made as a reflector for example or radiation blocker. This reflector or radiation blocker stops radiation from one scintillator layer being detected by the photodiode array associated with the other scintillator layer. If reflectors are used then these can be used for both layers and maximize the amount of radiation emitted in the direction of the associated photodiode array for that scintillator layer.

The first light emitting layer being positioned below the first photodiode array does not preclude another element of the X-ray detector being between the first light emitting layer and the first photodiode array.

The second light emitting layer below the second photodiode array does not preclude another element of the X-ray detector being between the second light emitting layer and the second photodiode array.

In an example, the at least one light emitting layer comprises at least one glass or polymer plate. At least one light source is configured to generate the radiation that is emitted by the at least one light emitting layer.

In an example, the at least one light source can be at least one LED.

In an example, the at least one light source is positioned proximate to at least one edge of the at least one light emitting layer.

This means, that X-rays can interact with both scintillator layers without having light sources such as LEDs in the X-ray path.

In an example, the at least one edge of the at least one light emitting layer is mirrored.

In this manner, light escaping from one or more sides of the at least one light emitting layer is minimized, thereby maximizing light emitted towards photodiode arrays.

Here mirrored means that the at least one edge can be supplied with a reflective coating, or given a mirror finish.

In an example, at least one face of the at least one light emitting layer substantially perpendicular to the at least one edge is roughened.

In this way, light coupling out of the surface or surfaces of the at least one light emitting layer towards the photodiode arrays can be enhanced.

In an example, the at least one LED is integrated into the at least one light emitting layer.

In an example, the at least one light emitting layer comprises at least one OLED layer.

In an example, a first surface of the first photodiode array faces the first scintillator layer and a second surface of the first photodiode array faces away from the first scintillator layer and a first surface of the second photodiode array faces the second surface of the first photodiode array. A first electrode is in contact with the second surface of the first photodiode array and a second electrode is in contact with the first surface of the second photodiode array.

In this manner, electrodes that are used as part of the biasing potential for the photodiode arrays can also be used as part of the power supply for light emitting means such as LEDs associated with the at least one light emitting layer.

In an example, the first electrode and second electrode are in contact with the at least one light emitting layer.

In a second aspect, there is provided an X-ray detector system, comprising an X-ray detector according to the first aspect; and a processing unit configured to control the X-ray detector such that the at least one light emitting layer does not emit radiation when the X-ray source is emitting X-rays.

In a third aspect, there is provided an X-ray detector system, comprising an X-ray source; and an X-ray detector according to the first aspect. Optionally, the X-ray detector system may also include the processing unit configured to control the X-ray detector such that the at least one light emitting layer does not emit radiation when the X-ray source is emitting X-rays.

Thus, the light emitting layer can operate continuously, however the photodiode arrays can generate an offset current when the X-ray sources operating that can be considered as a source of noise, however now the light emitting layer operates to mitigate the effect of defects only when the X-ray source is not operating. In other words, the light emitting layer(s) do(es) not provide illumination to the photodiode arrays during X-ray radiation, and can otherwise be permanently on.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
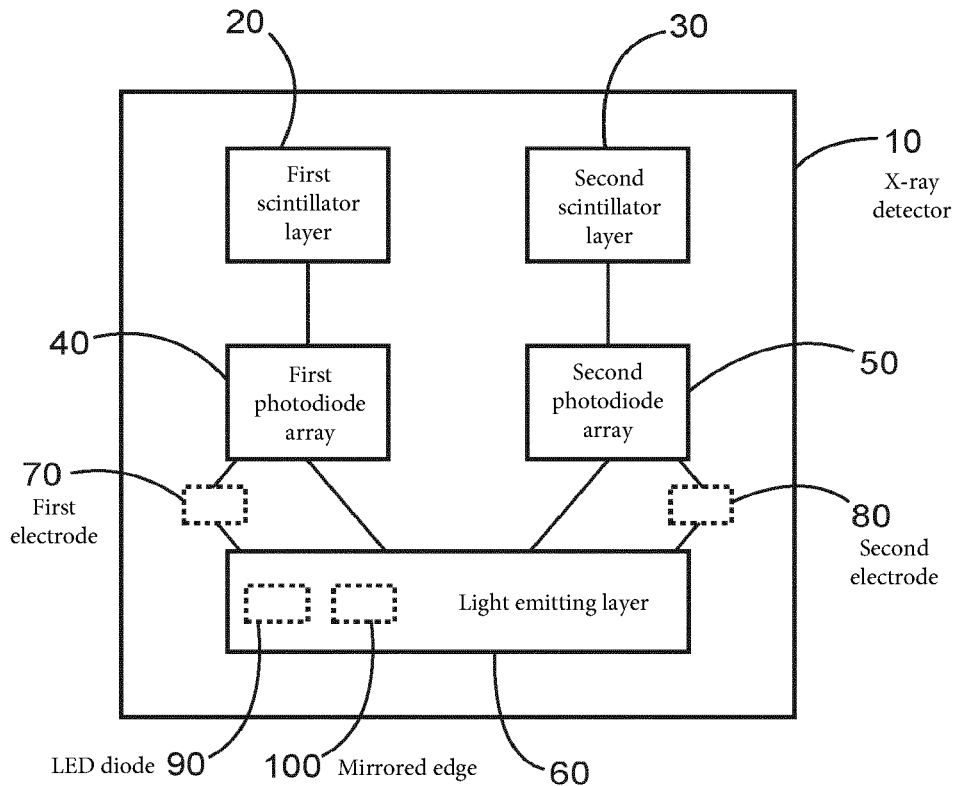
FIG. 1 shows a schematic set up of an example of an X-ray detector.

FIG. 1 shows an example of an X-ray detector 10. The X-ray detector comprises a first scintillator layer 20, a second scintillator layer 30, a first photodiode array 40, a second photodiode array 50, and at least one light emitting layer 60. The first scintillator layer is configured to absorb X-rays from an X-ray pulse and emit light. The first photodiode array is positioned adjacent to the first scintillator layer. The first photodiode array is configured to detect at least some of the light emitted by the first scintillator layer. The second scintillator layer is configured to absorb X-rays from the X-ray pulse passing through the first scintillator layer and emit light. The second photodiode array is positioned adjacent to the second scintillator layer. The second photodiode array is configured to detect at least some of the light emitted by the second scintillator layer. The at least one light emitting layer is configured to emit radiation. The at least one light emitting layer is configured such that at least some of the emitted radiation from the at least one light emitting layer irradiates the first photodiode array and at least some of the emitted radiation from the at least one light emitting layer irradiates the second photodiode array.

In an example, the at least one light emitting layer has a thickness no greater than 0.5 mm.

In an example, the at least one light emitting layer has a thickness no greater than 0.3 mm.

In an example, the at least one light emitting layer comprises at least one light plate.

According to an example, the at least one light emitting layer is configured to emit radiation at infrared wavelengths, and/or the at least one light emitting layer is configured to emit radiation at visible and/or the at least one light emitting layer is configured to emit radiation at ultraviolet wavelengths.

In an example, the visible and/or UV radiation is below 750 nm.

In an example, the infrared radiation is above 750 nm.

The skilled person would appreciate that these number are merely representative, thus for example visible and ultraviolet can in some cases be considered to be below 800 nm, and infrared can in some case be considered to above 800 nm or indeed above 900 nm.

According to an example, the at least one light emitting layer is positioned between the first photodiode array and the second photodiode array.

According to an example, the at least one light emitting layer is configured such that a transmission of the at least one light emitting layer in a direction from the first photodiode array to the second photodiode array for light emitted by the first scintillator layer is less than 10%, preferable less than 5%, more preferably less than 1%.

According to an example, the at least one light emitting layer is configured such that a transmission of the at least one light emitting layer in a direction from the second photodiode array to the first photodiode array for light emitted by the second scintillator layer is less than 10%, preferable less than 5%, more preferably less than 1%.

Figure 7:
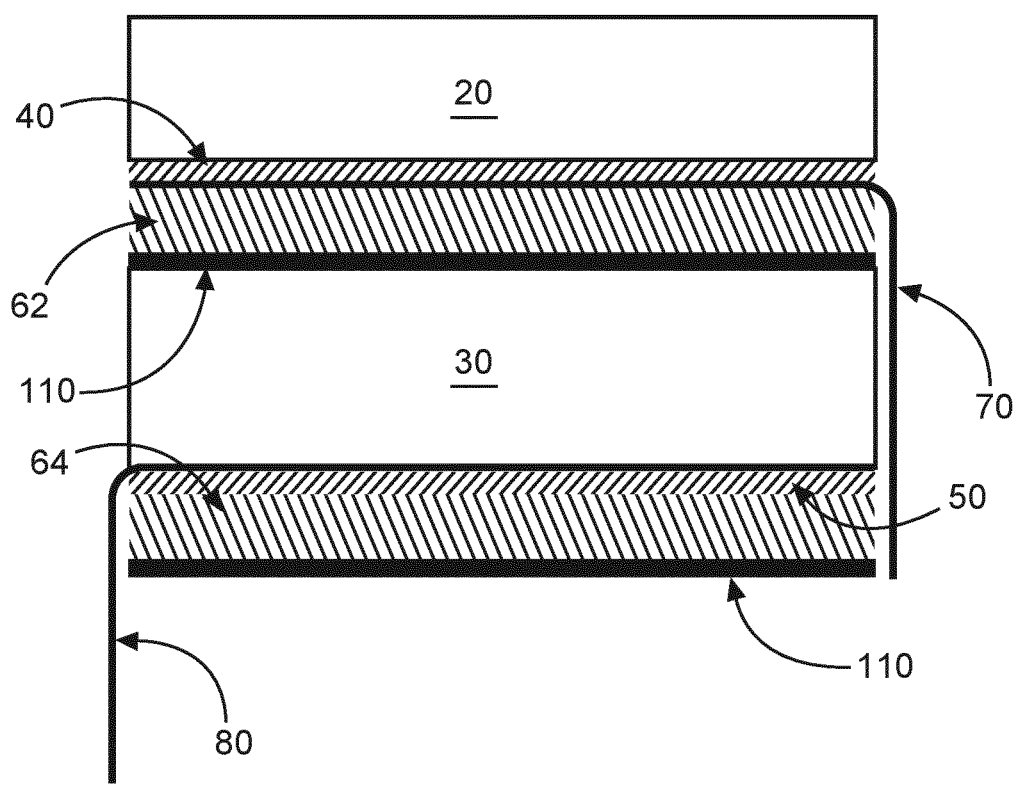
FIG. 7 shows a schematic set up of an example of an X-ray detector.

According to an example, a first layer 62 of the at least one light emitting layer is positioned below the first photodiode array and a second layer 64 of the at least one light emitting layer is positioned below the second photodiode array. FIG. 7 described below shows a possible embodiment of this example.

According to an example, the at least one light emitting layer comprises at least one glass or polymer plate, and at least one light source 90 is configured to generate the radiation that is emitted by the at least one light emitting layer.

The at least one light source can be at least one light emitting diode (LED).

According to an example, the at least one light source is positioned proximate to at least one edge of the at least one light emitting layer.

The at least one light source, such as one or more LEDs, can be external to a layer, transmitting light into layer, or can be embedded within the layer near to the edge of the layer.

According to an example, the light sources (e.g. LEDs) are within the light emitting layer and at least one edge of the at least one light emitting layer is mirrored 100.

However, light sources (e.g. LEDs) can be external to a layer injecting light into the layer to an edge that is not mirrored, whilst other edges of the layer can be mirrored.

According to an example, at least one face of the at least one light emitting layer substantially perpendicular to the at least one edge is roughened.

According to an example, the at least one light source such as at least one LED is integrated into the at least one light emitting layer.

According to an example, the at least one light emitting layer comprises at least one organic light emitting diode (OLED) layer.

According to an example, a first surface of the first photodiode array faces the first scintillator layer and a second surface layer of the first photodiode array faces away from the first scintillator layer and a first surface of the second photodiode array faces the second surface of the first photodiode array, and wherein a first electrode (70) is in contact with the second surface of the first photodiode array and a second electrode (80) is in contact with the first surface of the second photodiode array.

According to an example, the first electrode and second electrode are in contact with the at least one light emitting layer.

Figure 2:
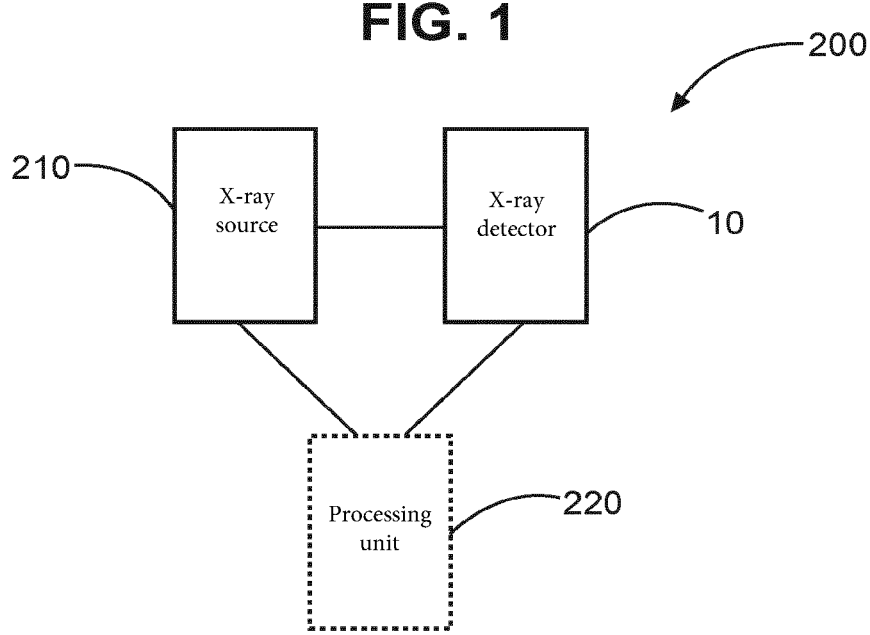
FIG. 2 shows a schematic set up of an example of an X-ray detector system.

FIG. 2 shows an example of an X-ray detector system 200. The X-ray detector system comprises an X-ray source 210, and an X-ray detector 10 as described above with respect to FIG. 1.

According to an example, the X-ray detector system 200 comprises a processing unit 220. The processing unit is configured to control the X-ray detector such that the at least one light emitting layer does not emit radiation when the X-ray source is emitting X-rays.

Thus for example, LEDs producing the light that is emitted by the at least one light emitting layer are controlled so as not to emit light when the X-ray source is emitting X-rays.

The X-ray detector and X-ray detector system are now described in further detail relating to specific embodiments, where reference is made to FIGS. 3-7.

Low cost photodiodes (based on organic layer—OPD—or a-Si) can now be used to replace expensive photodiodes in CT, through the special X-ray detector configuration described here. Thus, OPDs can now also considered for next generation dual-layer flat X-ray detectors. Up until now, these types of photodiodes arrays (PDA), albeit cost effective, have suffered from a number of artifacts which have hindered their adoption in these applications, particularly that for CT.

To set the scene, relating to the problem addressed by the current X-ray detector configuration, the following provides further details relating to the problems associated with low-cost photodiodes arrays. The most relevant non-ideal behavior relates to the PDA temporal characteristics. The effective gain (or detective efficiency) and the step response may appear to change over time due to charge trapping in the active area. Since these photodiodes can have a relatively high defect density in the bulk, charge can be trapped at the defect sites and only released at a comparatively very long time scale. This can cause ghosting-like artefacts, but also image artefacts, e.g. band artefacts in CT. Methods to counteract the temporal artefacts due to charge trapping are known, e.g. switching off bias; or short forward biasing intervals. Solutions for dual-layer detector applications involving bias light/backlighting have however up until now been lacking.

As discussed above, and providing more detail below, the present detector addresses this through a special arrangement of layers with one or more light emitting layers within detector arrangement used for "backlighting" of low-cost photodiode arrays used to detect radiation emitted from scintillator layers, where such low-cost photodiode arrays can be based on OPD or a-Si.

The inventors realized that by using a light wavelength with energy above the material bandgap (i.e. red light below 800 nm, the defect sites in the photodiode arrays used within the X-ray detector can be filled prior to X-ray illumination. Having filled the traps, it implies that no further trapping may occur and no changes of the detection efficiency may be perceived during the X-ray illumination. Furthermore, by doing so before every X-ray scan, it ensures that the same initial conditions are met for every image task. Furthermore, the inventors realized that illumination in the infrared sub-band (e.g. IR>900 nm) can also be used in order to fill traps within the bandgap.

It is however to be noted, that such pulsed operation of light emission within the new detector is not essential, and continuous backlight illumination can be considered. Here, the red and/or infrared illumination can remain on all the time. This can however also mean that the photodiode generates an offset current corresponding to the responsivity to the light, which may be considered as a source of noise. In this event, the pulsed backlight illumination as discussed above finds utility, where the illumination is switched off during the X-ray irradiation, and otherwise permanently on.

Figure 3:
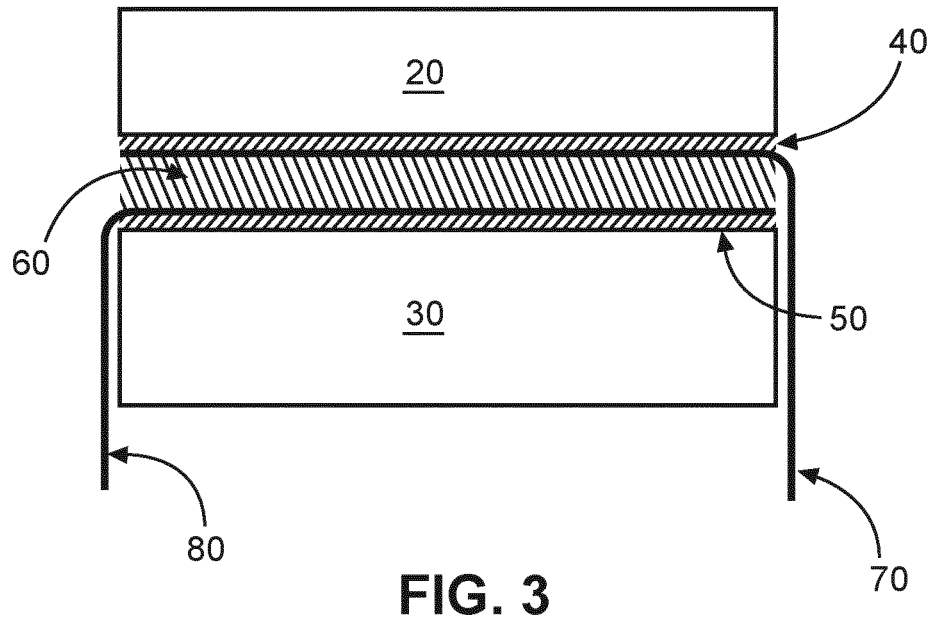
FIG. 3 shows a schematic set up of an example of an X-ray detector.

FIG. 3 shows an example of the new type of X-ray detector 10. The X-ray detector has a top layer scintillator 20, with a low-cost photodiode array 40 positioned adjacent to the top layer scintillator to detect radiation emitted from the scintillator resulting from the absorption of X-rays. The X-ray detector also has a bottom layer scintillator 30, with another low-cost photodiode array 50 positioned adjacent to the bottom layer scintillator detect radiation emitted from the scintillator resulting from the absorption of X-rays. A glass plate 60 is introduced between both photodiode arrays, which acts as a light emitting layer 60. The plate has integrated LEDs 90 and it serves as a diffusion plate such that the two PDAs are homogenously illuminated, thereby filling the defect sites and/or filling traps depending upon the wavelength of emission of the LEDs as discussed above. Other materials alternative to glass can be used for example, thick polymers, PMMA, etc. Thus the glass plate 60 acts as a mechanical support and infrared and/or red light, diffusion based light emitting layer.

In FIG. 3 the electrodes 70 and 80 are flex foil electrodes (base substrate material) which are sufficiently transparent to let most of the IR illuminate the photodiode arrays. In the configuration shown in FIG. 3, the PDAs can be taken to be "back" illuminated by the light emitting layer 60 (for light proceeding from the scintillator layer). Alternatively, the flex foil may be on top of the PDA (front-illuminated type) and it only requires being optically transparent (e.g. ITO routing). In this alternative configuration (see FIG. 4), the glass plate is in direct contact with the PDA.

A benefit of the embodiment shown in FIG. 3, is that the flex substrates (flex foil electrodes) can carry the supply voltage to the LEDs of the glass plate as well as provide bias voltages to the PDAs. Since the glass plate is "sandwiched" between two flex foils, each foil can carry one of the supplies, e.g. common cathode top and common anode bottom, or vice versa.

The glass can cause some undesirable X-ray absorption. It is therefore of benefit that the glass substrate be kept as thin as possible. Ideally, it should not be thicker than 0.5 mm, preferably thinner than 0.3 mm.

Figure 4:
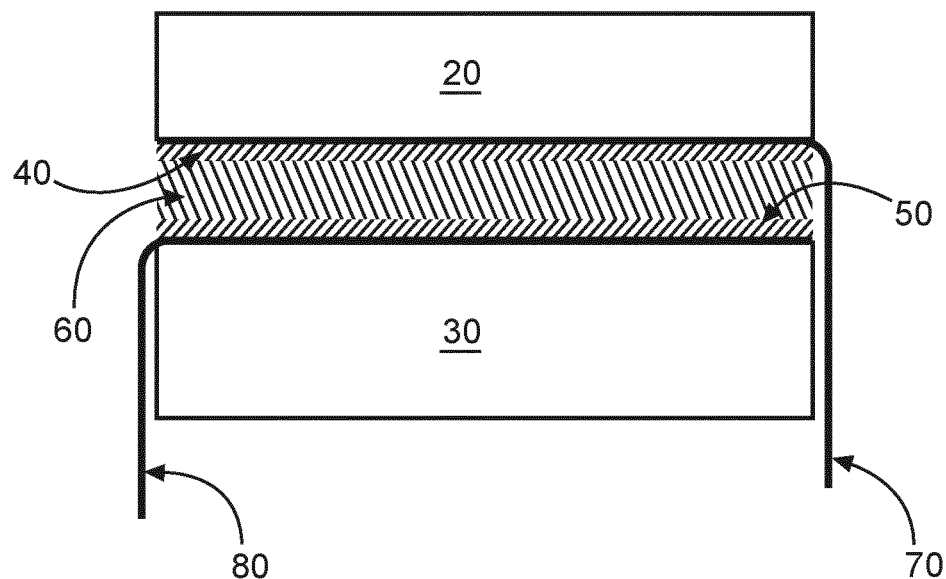
FIG. 4 shows a schematic set up of an example of an X-ray detector.

Regarding, the embodiments shown in FIGS. 3 and 4, due to the almost transparent nature of the PDA (particularly OPD), light crosstalk can occur across both scintillator layers, deteriorating the energy separation of the dual layer detector. To address this, the glass surfaces can be treated to have a transmission, across the interface, of for example only 10%. The remaining light can be reflected and/or absorbed. With a 10% transmission on each glass surface/interface, the crosstalk across both layers is constrained to well below 1%, since light trying to travel from one scintillator layer to the other scintillator layer's photodiode array will have to cross two successive interfaces with 10% transmission. The LED array providing radiation for the glass light emitting layer, in such a situation may need to provide more light to compensate for the lack of transmission at the exit surfaces of the glass layer. The flex foil electrodes for as shown in FIG. 4 are now positioned between the photodiode arrays and the scintillator layers.

Figure 5:
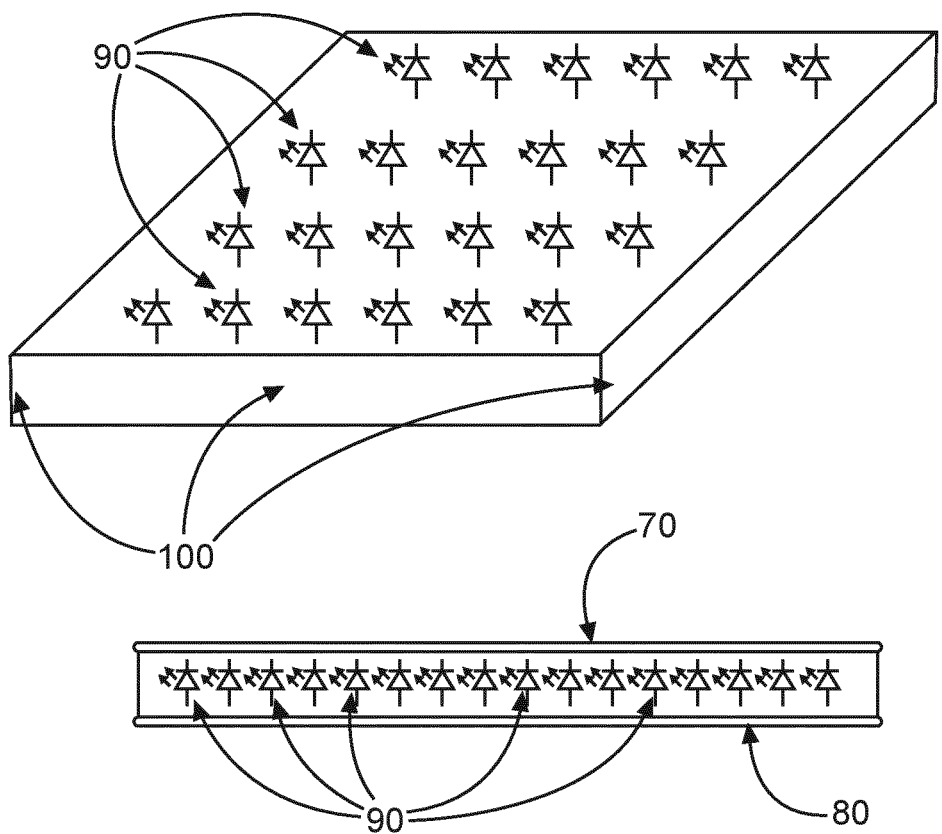
FIG. 5 shows a schematic set up of an example of a light emitting layer of an example of an X-ray detector.
Figure 6:
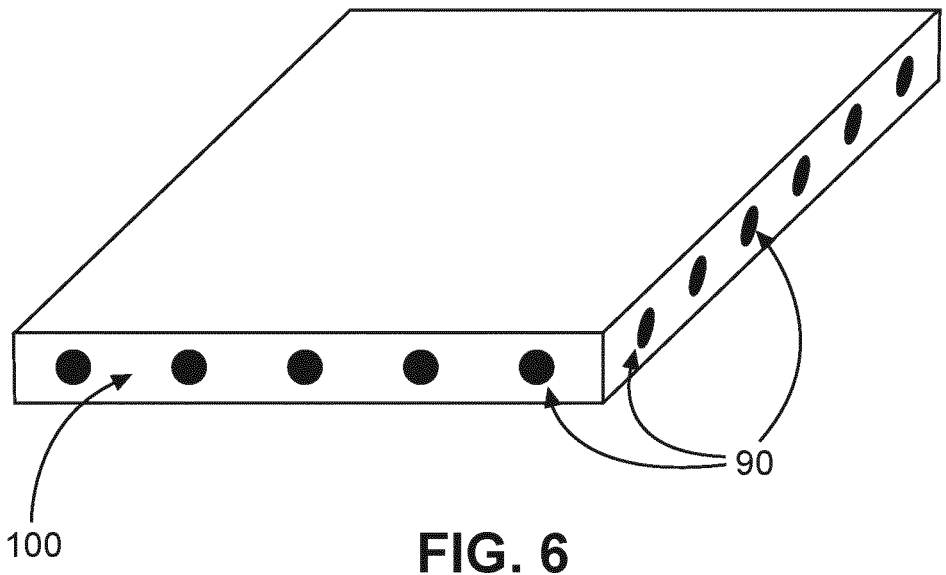
FIG. 6 shows a schematic set up of an example of a light emitting layer of an example of an X-ray detector.

FIGS. 5 and 6 show examples of exemplary glass plates. Preferably all or most of the edge sides of the glass plates are cladded with a reflective material such that the light emitted by both top and bottom surfaces is maximized. Thus, the glass plate has reflective or mirrored edges 100 for example a mirror or $TiO_2$ (from the inner side).

In the embodiment shown in FIG. 5, the LED diodes 90 are integrated into the glass plate. In this embodiment, the electrodes 70, 80 can be a uniform electrode on the bottom/top, however each LED can have a "dot" contact on both sides and be contacted individually.

In the embodiment shown in FIG. 6, the LED diodes 90 are placed only at the sides of the glass plate to maximize the edge mirror coverage, i.e. reflected light on the edges is not absorbed by the LED array in the glass volume. In this case the LEDs are also not in the X-ray path for the lower layer detector. The top and bottom surface of the glass layer can be roughened to enhance out-coupling of light from the LEDs via scattering. The roughening of surfaces can also apply to the embodiment shown in FIG. 5.

In flat detectors, the existing glass plate can be used to couple light from the sides. The bottom surface of the plate may be treated to increase light scatter and produce a homogenous light distribution across the detector.

In the above embodiments the glass plate is placed in between and serves both photo diode layers. Alternatively, each photodiode array may have its own light emitting layer or plate. In this case, crosstalk across layers can be minimized or even completely eliminated, at the expense of a slightly more complicated stack. FIG. 7 shows an example of this implementation. It must be noted however, that for flat panel applications, the bottom back-illumination may already be available. In this case the stack can again consist of a single glass plate sandwiched between both layers, however only serving the top layer. As it can be seen in FIG. 7, now the inner glass plate is equipped with a reflector 110 on its bottom side, maximized the use of light and helping prevent light crosstalk across layers. However, rather than a mirror this layer could just be a radiation blocking layer for UV/visible/infrared, whilst being not overly attenuating to X-rays. It is to be noted that the embodiment shown in FIG. 7 is just one of a number of possible arrangements. For example the top layer can be a back-illuminated BIP PDA and the bottom layer can be a front-illuminated FIP. However, the top layer can be a FIP, with the bottom layer a BIP. However, both layers can be BIP or both layers can be FIP. Also, any of the arrangements of layers discussed above with respect to FIG. 7 can be reversed, in that rather than X-rays coming from top of the figures, X-rays can come from the bottom.

As discussed above, the flex foil electrodes 70, 80, shown in the embodiment of FIG. 3 and indeed in the embodiment shown in FIG. 7 can carry supply voltages to the LEDs of the glass plate as well as provide voltages to the photodiode arrays. The flex foil electrodes for the X-ray detector as shown in FIG. 4 are now positioned between the photodiode arrays and the scintillator layers, and as such a different technique is required to bias the light emitting glass plate. There are several mechanisms how this can be accomplished:

The photodiode arrays can have a substrate (also called bulk) contact on top. That is, the substrate (bottom side) of the photodiode array can be biased to a certain potential from a top contact. The other photodiode array can then to be biased to a different potential sufficient to drive the LEDs associated with the glass plate. That is, the bottom side of the photodiode arrays can provide the biasing.

The photodiode arrays have TSV (through silicon vias) contacts bringing a dedicated bias voltage from top to bottom (mirrored for FIG. 4) and give access to the glass plate. In this case, it can be sufficient that only one array provides both potentials to the plate, which is particularly suitable if the plate has contacts only on one side. (For the embedded LED case the contacts can be on both sides). Because the photodiode arrays are typically very thin, TSVs are compatible.

The flex foil (top layer) can make contact to the side of the plate. This is particularly suited when LEDs are placed on the side of the glass plate, but it is not restricted to this embodiment.

The glass plate can have a dedicated flex foil coming out of a 3$^{rd}$ side (or two sides).

It is also to be noted that an embodiment of the X-ray detector can in effect be a combination of the embodiments shown in FIG. 3 and FIG. 4 is in principle possible. In this combined embodiment, the top layer can be back-illuminated and provide the bias for the plate through the flex foil only from one side. The bottom layer can then be any type of photodiode array with no need for contacting the plate.

For the embodiments discussed above, the flex foils are therefore acting as an interconnect to the photodiode array electrodes and can also provide the bias for the light emitting glass plate. This applies for the case where the X-ray detector is used in CT applications, where the full detector is composed of tiles, i.e. the detector consists of smaller elements arranged adjacent to each other resulting on a large area detector. However, this also applies for X-ray detectors for other X-ray applications. In this latter case, large area devices find utility and the "flex foil" can be in the form of a TFT panel (Thin-Film transistor, flex or otherwise) which also provides the front-end read-out for the photodiode arrays. The TFT can then connect to line amplifiers and ADC on one or more sides.

In the above discussion, light emitting layer in the form of a glass plate with LEDs has been described, where it was mentioned that polymer rather than glass could be utilized. However, the light emitting layer, can be in the form of a thin electroluminescent layer, such as an organic light emitting diode OLED layer.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray multi-layer detector, comprising:
   a first scintillator layer configured to absorb X-rays from an X-ray pulse and to emit light;
   a second scintillator layer configured to absorb the X-rays from the X-ray pulse passing through the first scintillator layer and to emit light;
   a first photodiode array positioned adjacent to the first scintillator layer and configured to detect at least some of the light emitted by the first scintillator layer;
   a second photodiode array positioned adjacent to the second scintillator layer and configured to detect at least some of the light emitted by the second scintillator layer; and
   at least one light emitting layer configured to emit radiation and configured such that at least some of the emitted radiation irradiates the first photodiode array and at least some of the emitted radiation irradiates the second photodiode array.

2. The X-ray multi-layer detector according to claim 1, wherein the at least one light emitting layer is configured to emit radiation at infrared wavelengths, and/or the at least one light emitting layer is configured to emit radiation at visible wavelengths and/or ultraviolet wavelengths.

3. The X-ray multi-layer detector according to claim 1, wherein the at least one light emitting layer is positioned between the first photodiode array and the second photodiode array.

4. The X-ray multi-layer detector according to claim 3, wherein the at least one light emitting layer is configured such that a transmission of the light emitted by the first scintillator layer in a direction from the first photodiode array to the second photodiode array, and/or the transmission of the light emitted by the second scintillator layer in a direction from the second photodiode array to the first photodiode array is less than 10%.

5. The X-ray multi-layer detector according to claim 1, wherein the at least one light emitting layers comprises:
   a first light emitting layer; and
   a second light emitting layer,
   wherein the first light emitting layer is positioned below the first photodiode array and the second light emitting layer is positioned below the second photodiode array.

6. The X-ray multi-layer detector according to claim 1, wherein the at least one light emitting layer comprises at least one glass or polymer plate, and at least one light source configured to emit the radiation.

7. The X-ray multi-layer detector according to claim 6, wherein the at least one light source is positioned proximate to at least one edge of the at least one light emitting layer.

8. The X-ray multi-layer detector according to claim 7, wherein the at least one light emitting layer comprises at least one roughened face substantially perpendicular to the at least one edge.

9. The X-ray multi-layer detector according to claim 6, wherein the at least one light emitting layer comprises at least one mirrored edge.

10. The X-ray multi-layer detector according to claim 6, wherein the at least one light emitting layer comprises at least one LED.

11. The X-ray multi-layer detector according to claim 1, wherein the at least one light emitting layer comprises at least one OLED layer.

12. The X-ray multi-layer detector according to claim 1, further comprising:
   a first electrode; and
   a second electrode, wherein a first surface of the first photodiode array faces the first scintillator layer, and a second surface of the first photodiode array faces away from the first scintillator layer, and a first surface of the second photodiode array faces the second surface of the first photodiode array, and wherein the first electrode is in contact with the second surface of the first photodiode array, and the second electrode is in contact with the first surface of the second photodiode array.

13. The X-ray multi-layer detector according to claim 12, wherein the first electrode and the second electrode are in contact with the at least one light emitting layer.

14. An X-ray detector system, comprising:
   an X-ray source for emitting X-rays; and
   an X-ray multi-layer detector according to claim 1.

* * * * *